US010595939B2

(12) United States Patent
Jones et al.

(10) Patent No.: US 10,595,939 B2
(45) Date of Patent: Mar. 24, 2020

(54) SKIN TREATMENT APPARATUS UTILISING INTENSE PULSED LIGHT (IPL)

(71) Applicant: iPulse Limited, Swansea (GB)

(72) Inventors: Stuart Terry Jones, Swansea (GB); Daniel Colin Farr, Cardiff (GB)

(73) Assignee: iPulse Limited, Swansea (GB)

( * ) Notice: Subject to any disclaimer, the term of this patent is extended or adjusted under 35 U.S.C. 154(b) by 27 days.

(21) Appl. No.: 15/101,102

(22) PCT Filed: Dec. 4, 2014

(86) PCT No.: PCT/GB2014/053609
§ 371 (c)(1),
(2) Date: Jun. 2, 2016

(87) PCT Pub. No.: WO2015/082928
PCT Pub. Date: Jun. 11, 2015

(65) Prior Publication Data
US 2016/0374758 A1  Dec. 29, 2016

(30) Foreign Application Priority Data

Dec. 4, 2013 (GB) .................................. 1321382.2

(51) Int. Cl.
A61B 18/18 (2006.01)
A61N 5/06 (2006.01)
A61B 18/00 (2006.01)

(52) U.S. Cl.
CPC ............ *A61B 18/18* (2013.01); *A61N 5/0616* (2013.01); *A61B 2018/00476* (2013.01);
(Continued)

(58) Field of Classification Search
CPC .......... A61B 18/18; A61B 2018/00642; A61B 2018/1807; A61B 2018/00476;
(Continued)

(56) References Cited

U.S. PATENT DOCUMENTS 4,853,600 A  8/1989 Zeltner et al.
5,720,772 A  2/1998 Eckhouse
(Continued)

FOREIGN PATENT DOCUMENTS

EP  0885629 A2  12/1998
EP  1658113 A1  5/2006
(Continued)

OTHER PUBLICATIONS

Search report issued in co-pending international application No. PCT/GB2014/053609, dated Jun. 8, 2015.
(Continued)

*Primary Examiner* — Rex R Holmes
(74) *Attorney, Agent, or Firm* — Dinsmore & Shohl LLP

(57) ABSTRACT

The present invention relates to an apparatus for treating skin by means of intense pulsed light (IPL). Such apparatus may be used for the treatment of, for example, cosmetic purposes such as hair depilation or dermatological treatment of skin conditions such as acne or rosacea. The present invention provides an improved apparatus that can be used by a non-medical practitioner and comprises a light source comprising a light emitting element for transmitting light energy to the skin and a charge storage device for discharging an energy dose to the light emitting element. There is further provided at least one sensor for measuring a parameter of the skin and a control system configured to determine the treatment energy dose to be delivered. This treatment energy dose is derived using the sensor measurement and means of reduction in unwanted time delay associated with charging or discharging of the charge storage device in sole dependence on the current or most recently measured skin parameter.

23 Claims, 10 Drawing Sheets

(52) U.S. Cl.
CPC ........ *A61B 2018/00642* (2013.01); *A61B 2018/00702* (2013.01); *A61B 2018/00708* (2013.01); *A61B 2018/00785* (2013.01); *A61B 2018/1807* (2013.01); *A61N 2005/0627* (2013.01); *A61N 2005/0644* (2013.01)

(58) Field of Classification Search
CPC ........ A61B 2018/00702; A61B 2018/00785; A61B 2018/00708; A61N 5/0616; A61N 2005/0644; A61N 2005/0627
See application file for complete search history.

(56) References Cited

U.S. PATENT DOCUMENTS

| | | | |
|---|---|---|---|
| 5,885,274 | A | 3/1999 | Fullmer et al. |
| 6,187,001 | B1 | 2/2001 | Azar et al. |
| 6,273,883 | B1 | 8/2001 | Furumoto |
| 2004/0167501 | A1* | 8/2004 | Island .......... A61B 18/203 606/9 |
| 2012/0116373 | A1* | 5/2012 | Moench ......... A61B 18/203 606/9 |
| 2014/0005756 | A1 | 1/2014 | Liu et al. |

FOREIGN PATENT DOCUMENTS

| | | | |
|---|---|---|---|
| EP | 2632548 A1 | 9/2013 | |
| GB | 2496895 | 5/2013 | |
| JP | 2007-502141 | 2/2008 | |
| JP | 2013223717 | 10/2013 | |
| WO | 02085229 A2 | 10/2002 | |
| WO | WO 2005015291 A2 * | 2/2005 | ........ A61B 18/18 |
| WO | 2007113817 A2 | 10/2007 | |
| WO | 2009021225 A1 | 2/2009 | |
| WO | WO-2013173516 | 11/2013 | |

OTHER PUBLICATIONS

Ancona, D. et al., "A multicentre trial of epilation efficacy of a new, large spot size, constant spectrum emission IPL device" Journal of Cosmetic and Laser Therapy, 2007: 9: 139-147.

Clement, M. et al., "Optimising the design of broad-band light source for the treatment of skin," *Journal of Cosmetic and Laser Therapy*, 2005, 7: 177-189.

Machine English translation of JP2007-502141.

* cited by examiner

SKIN TREATMENT APPARATUS UTILISING INTENSE PULSED LIGHT (IPL)

REFERENCE TO RELATED APPLICATIONS

This application is a U.S. national stage application of PCT/GB2014/053609, filed Dec. 4, 2014, which claims priority from Great Britain patent application No. GB1321382.2, filed Dec. 4, 2013. The entire content of both of which is incorporated herein by reference.

FIELD OF THE INVENTION

The present invention relates to an apparatus for treating skin by means of intense pulsed light (IPL) and methods of treating the skin using intense pulsed light and use of such an apparatus.

BACKGROUND OF THE INVENTION

Skin treatment apparatus is known in the art for treatment of, for example, cosmetic purposes such as hair depilation, minimisation of skin blemishes or skin rejuvenation, as well as dermatological treatment of skin conditions such as acne or rosacea. The skin is exposed to dosages of radiation such as from a laser source or light source where the radiation is targeted to the skin and the energy intensity and pulse duration is controlled. In hair depilation, the radiation source is targeted to cause heating of the hair root causing the hair root to die.

Apparatus for use in treating the skin using intense pulsed light (IPL) in particular is now increasingly available for non-professional use, i.e., for the consumer market. Accordingly, there is an associated risk of side effects to the skin through misuse. This may be in the form of skin irritation and pain through the effect of burning or pigment change.

GB2496895 discloses an apparatus including a light source, a control unit and a base unit. The control unit removably docks from the base and comprises a sensor which can detect skin tone. This control unit is therefore positioned on the skin and detects the skin tone and is then replaced into the base unit wherein the base unit then determines the power level of radiation to be generated by the light source. The head unit (20) is then repositioned onto the skin at the location for which the skin tone has been determined and the skin is treated with a pulse of light without the requirement for the user to select an energy level output. This means that the step of the user selecting the energy to be output from the light source is removed thus reducing the potential harmful effect of a user misusing the apparatus.

WO02/085229 also discloses a device for treating skin by means of radiation pulses such as a laser source. The aim of the invention disclosed in WO02/085229 is again to reduce undesirable side effects on the skin such as skin irritation and pain through misuse of the device. This is achieved through detecting a biophysical property of the skin such as the skin tone. The device comprises a housing (3) which is portable and can be placed on or moved over skin (7) to be treated. The housing (3) accommodates a radiation source, in particular a laser source (9) such as a laser diode. The housing is positioned on the skin and an image is recorded of the part of the skin situations directly in front of an exit opening (15). The positions of the hair root (39) of the hairs (41) are determined and the laser source (9) is manipulated in order that the hair roots (39) are successively heated in such a manner that they die. Protection against an impermissible overdose of the laser pulse, however, is achieved by using a detector (43) which detects, for example, the temperature of the skin resulting from exposure to a series of test laser pulses. The detector measures the temperature of the skin after each pulse to ensure that a maximum temperature is not exceeded. In such a manner the permissible dose of energy from a laser source is controlled.

WO02/085229 discloses a further embodiment wherein a detector is utilised which measures the scattering coefficient and/or absorption coefficient of the skin for light of a predetermined wavelength and the pulse dose is determined by means of the scattering coefficient and/or absorption coefficient of the skin.

There are problems associated with the prior art arrangements. GB2496895 determines the light energy pulse dependent upon skin tone, however, relies on a user then repositioning a treatment head onto a correct location for which the skin tone has been determined. It is unlikely that positioning of the treatment head accurately reflects the positioning of the detector thus giving the possibility of incorrect output energy. Further, there is significant time delay between sensing the skin tone and the time of the treatment. WO02/085229 overcomes the problem of inaccurate positioning of the treatment head by utilising a head which incorporates both a detector for detecting a parameter of the skin such as temperature, scattering coefficient and/or absorption and treats the skin dependent on this outcome. Whilst this is possible when utilising a laser pulse there are distinct safety issues associated with the use of laser pulses.

Referring to FIGS. 1A-1C a prior art system is schematically presented as a block diagram showing how an IPL system functions. FIG. 1A identifies components in a prior art system and includes an energy storage device (20), typically comprising a capacitor, is arranged to release energy to the flashlamp (22) which in turn outputs a pulse of light energy to the skin under operation of the lamp trigger circuit (24). The energy storage device (20) is charged by a charge circuit (26) where the charge circuit (26) and lamp trigger circuit (24) are under operation of the control circuit (28). A user input (30) is provided such as a trigger which is depressed to enable the control circuit (28) to cause actuation of the lamp trigger circuit (24) causing release of charge from the energy storage device (20) to the flashlamp (22). In order to control the value of energy stored by the energy storage device (20) an input is provided to the control circuit (28) which is either from a sensor (32) arranged to measure a skin parameter such as skin tone as represented in FIG. 1A or by a user selected input described in more detail with respect to FIG. 1B.

Represented in FIG. 1B is a schematic representation of the change over time of the light output, the user input, the capacitor voltage and the capacitor charging. Prior to time T1 a user turns the apparatus on and the output power required for treatment of the skin is determined. In most prior art systems this is determined by a user visually comparing their skin tone against a chart and manually selecting a power level. In GB2496895 this is determined by a control unit having a sensor to determine the preferred power output dependent on the skin tone thereby removing the requirement for the user to make a comparison with a known scale. At T1 the control circuit (28) charges the capacitor during which time the capacitor voltage increases until T2 is reached. The time between T2 and T3 represents the time in which the capacitor is charged until the user operates the user input (30) between T3 and T4. At T4 the charge on the capacitor is released to the flashlamp and the light pulse is released onto the skin as represented by the curve between T4 and T5. The cycle is repeated as necessary on another area of skin.

FIG. 1C presents the change in light intensity over time dependent on the power output required. As such if the sensor or manual user input requires a power output of 7 J/cm$^2$ then the capacitor is charged to 400V. Alternatively, if the skin tone is fair or light, then an energy output of 5 J/cm$^2$ may be more appropriate and the capacitor is charged to a voltage of 338V.

The applicant has realised that there are significant limitations associated with prior art arrangements. The significant time delay associated with sensing a skin parameter such as the skin tone, subsequently charging the capacitor on the basis of the skin tone and causing energy release from the capacitor gives a significant delay to a user causing uncertainty in a user's mind as to whether the apparatus is actually operated correctly and further meaning that it is possible and likely that the apparatus has actually been moved relative to the skin before the energy pulse is discharged. This could lead to safety implications where the device was removed from the skin and was still enabled to discharge the energy. Accordingly, as described in FIG. 2, the applicant has determined that the capacitor voltage could be changed continuously or at regular time intervals on the basis of a changing measured sensor output whereby the skin tone reading is continuously or regularly being taken. This means that the effect of a user moving the apparatus before actuation of the user input would be mitigated. This would also mean that the energy stored ready for discharge by the energy storage device would be continuously adjusted, (charged or discharged) corresponding to the latest skin tone reading. This is presented in FIG. 2 showing how the sensor measures different skin tone across the skin.

SUMMARY OF THE INVENTION

As presented in FIG. 2 there is continuous (meaning repeating or regular) sensor measurement between the time that the apparatus is switched on at T0 following which a valid sensor measurement is taken. On the basis of this sensor measurement the capacitor charging starts at T1 and as shown, the capacitor voltage increases up until a voltage is achieved at T2 corresponding to the sensor measurement at that time. As the sensor measurement then identifies that a lower energy output from the flashlamp is required the capacitor ceases to charge between time T2 and T3 and during this time residual energy left in the capacitor is released thus enabling the capacitor voltage to decrease. Between time T3 and T4 again the capacitor is charged due to the sensor measurement identifying that a greater energy output is required the capacitor voltage increases. The user input is then activated at T4. However, the sensor measurement is recorded at T5 and the sensor measurement identifies that the required energy output should be less than would be achieved by the stored energy or the capacitor at that time. Accordingly, at T5 the capacitor charging ceases and the capacitor voltage is decreased. During the time between T5 and T6 the user input has been actuated, however, the capacitor voltage must decrease. The problem with this is that reduction of the capacitor voltage to reflect the required output for the current sensor measurement takes significant time which may be, for example, between three to ten seconds. This is undesirable in an automated system wherein the energy output is dependent on a sensor output as again it may lead to further movement of the apparatus on the skin thereby creating further delays to further sensor measurements being recorded and again would cause difficulties for a user in knowing when the apparatus was functioning correctly.

The present invention provides an improved apparatus that can be used by an individual who is not a medical practitioner thus ensures fast, effective treatment without any of the safety implications or disadvantages identified above.

According to an aspect of the present invention there is a skin treatment apparatus comprising:
- a light source comprising a light emitting element for transmitting light energy to the skin and a charge storage device for discharging an energy dose to the light emitting element;
- at least one sensor for measuring a parameter of the skin;
- a control system configured to determine a treatment energy dose to be delivered, this being derived using the sensor measurement; and
- i) wherein the control system is arranged to terminate discharge of the charge storage device upon delivery of the treatment energy dose; and/or
- ii) wherein the charge storage device comprises a plurality of individual charge storage elements, and the control system is arranged to control discharge of the plurality of individual charge storage elements to deliver the treatment energy dose; and/or
- iii) wherein the control system is arranged to enable charging of the charge storage device in a two or more stage operation, wherein in a first stage charging is to an intermediate energy level, and in a second or further stage to an energy level sufficient to deliver the treatment energy dose; and/or
- iv) wherein the control system is arranged to modulate discharge of the charge storage device to deliver the treatment energy dose.

The claimed invention (and the alternative aspects defined) provide an extremely beneficial system where in each aspect the technical problem of unwanted time delay associated with charging or discharging of the charge storage device in sole dependence on the current or most recently measured skin parameter such as skin tone is removed. This speed means there is little possibility of significant movement of the apparatus between sensing a skin parameter and carrying out the treatment. Furthermore, usability is significantly improved as a user will not have any uncertainty as to whether the treatment has occurred as there will be substantially zero time delay between user activation to cause treatment and delivery of the treatment energy dose.

In one aspect the apparatus is preferably a hair depilation apparatus.

In one aspect the control system is arranged to terminate discharge of the charge storage device upon delivery of the treatment energy dose and/or before discharge is complete. This is beneficial as the discharge can be terminated as necessary to deliver only the treatment energy dose. This further means that the charge storage device can be charged independently of the sensor measurement of the treatment area. Control of the energy supply to the skin is therefore effectively controlled upon release. This is rather than being controlled upon energy supplied to the charge storage device. As such, charging of the charge storage device can be completed quickly and there is no requirement to release charge from the charge storage device due to the energy stored thereon being too high. The charge storage device can be charged to a voltage that may be the same each time the apparatus is used.

It will be appreciated that the treatment energy dose may be controlled upon release from the charge storage device, so the treatment energy dose may be free discharge of the charge storage device and/or a modulated discharge that may extend the treatment time period. This means that the actual light intensity contacting the skin can be controlled, and the light output delivered over an extended time frame if required to reduce intensity for the user.

The treatment energy dose can be manipulated before discharge for example through a user input, thereby increasing or decreasing the treatment energy dose for example. However, it will be appreciated that the control system terminates discharge of the charge storage device once the treatment energy dose has been delivered where the treatment energy dose can be determined solely on the basis of the sensor measurement or to include an additional input such as a user input to provide improved efficacy for a specific user.

In one aspect the charge storage device comprises a plurality of individual charge storage elements, and the control system is arranged to control discharge of the plurality of individual charge storage elements to deliver the treatment energy dose. The control system is beneficially arranged to selectively discharge one or more of the plurality of charge storage elements to deliver the treatment energy dose. This means that one or more individual charge storage elements can be activated and preferably discharged independently of the other individual charge storage elements. For example, if two individual charge elements are provided, one charge element can be discharged independently of the other. If there are three charge element for example two charge elements can be discharged simultaneously or sequentially and the other left charged, or for example all three charge elements can be discharged again simultaneously, sequentially or a combination thereof, depending on the determined energy treatment dose. Again, this provides the benefit in that there is no delay associated with a user inputting their requirement to activate the apparatus and release the energy to the skin and this actually occurring. As such, control of the energy output to the skin is achieved through discharge of one or more individual charge storage elements. A plurality of charge storage elements may be charged, again preferably independently of the sensor measurement meaning that the output energy can be adjusted to the required treatment intensity with no time delay. It is beneficial that in order to achieve the desired energy output to the skin, two or more of the individual charge storage elements may be charged to different voltages. It will further be appreciated that the control system may be arranged to modulate discharge of energy from the plurality of charge storage elements.

In a further aspect the control system is arranged to enable charging of the charge storage device in a two or more stage operation, wherein a first stage charging is to an intermediate energy level, and a second or further stage to an energy level sufficient to deliver the treatment energy dose. The charge storage device can therefore be effectively charged to a minimum voltage between energy doses supplied to the skin and the charge storage device may effectively be 'topped up' dependent on the sensor measurement. In such an embodiment there may be a small time delay between a user activating the apparatus to the treatment energy dose being supplied. In such an embodiment, the control system is arranged to partially charge the charge storage device dependent on the sensor measurement.

In one aspect the control system is arranged to modulate discharge of the charge storage device to deliver the treatment energy dose. This provides a further alternative means of ensuring that the correct treatment energy dose may be delivered to the light emitting element and subsequently to the user derived using the sensor measurement. An energy modulation arrangement is beneficially provided to modulate the supply of treatment energy dose to the light emitting element. The modulation arrangement beneficially comprises an electronic switch such as a Mosfet. Pulse width modulation or pulse duration modulation may be utilised to control discharge of the charge storage device meaning that the output light from the light emitting element can be manipulated. This means that the intensity of the light hitting the user's skin may be controlled, and may be changed over time. Utilising pulsed switch modulation effectively switches the discharge of the charge storage device from an 'off' to an 'on' configuration and the longer the switch is on compared to the off period, the higher the energy supplied to the light emitting element is meaning that the intensity of the light transferred to the user is increased. This means that again it is unnecessary to charge the charge storage device after receipt of a sensor reading. Unwanted time delay associated with charging or discharging of the charge storage device where dependence on the current measured skin parameter such as skin tone is removed.

The apparatus preferably further comprises a housing arranged to accommodate the light emitting element and the sensor. This means that accuracy of the sensed skin parameter with respect to the actual area of the skin treated is maintained. The light emitting element and sensor are preferably in fixed locations relative to each other as defined by the housing.

The apparatus preferably comprises an indicator for providing information regarding the sensor measurement and/or the treatment energy dose. The indicator is preferably a display. This provides a safety check in that the user will be provided with an indication of the sensor measurement and/or treatment energy dose meaning that operation of the apparatus can be stopped if the indication is deemed severely compromised.

The control system is beneficially arranged to control charging of the charge storage device prior to and/or at the same time as determination of the treatment energy dose. This means that there is no time delay associated with making a measurement of a parameter of the skin and subsequently charging the charge storage device. The control system is beneficially configured to enable charging of the charge storage device and/or one or more individual charge storage elements to a predetermined voltage.

In operation the sensor is beneficially arranged to record multiple skin parameter measurements prior to determination of the treatment energy dose. This means that the actual or correct skin treatment area for which a sensor reading is recorded is treated in the event, for example, that the user accidently moves the apparatus.

The control system is beneficially configured to determine the treatment energy dose based on a plurality of the multiple skin parameter measurements. As such the control system may continuously determine the necessary output treatment energy dose at the exact location on which the apparatus is positioned.

The control system is beneficially configured to control supply of the treatment energy dose to the light emitting element. This controlled supply of the treatment energy dose to the light emitting element may take a variety of forms and the controlled supply may be adjusted in that the energy pulse may be modulated. There is beneficially an energy modulation arrangement configured to modulate supply of the treatment energy dose to the light emitting element. The output energy treatment may therefore be controlled in terms of shape, meaning that, for example, a square energy pulse could be output thereby controlling the light intensity, contacting the user, and/or the time period of discharge could be changed, for example increased.

A discharge control element is beneficially provided arranged to terminate the energy supplied from the charge storage device. This is beneficially activated once the treatment energy dose is reached. This provides significant benefits. The charge storage device can be charged to a voltage that allows a potentially greater energy output to be released than actually required for the treatment energy dose. This may be predetermined and can always be the same value meaning that the requirement to be dependent on the sensor output for the treatment of the skin at that moment is removed as the energy supplied from the charge storage device can be terminated through provision of a discharge control element once the predetermined energy is released. Residual charge can be left on the charge storage device. The discharge control element beneficially comprises a switch beneficially comprising an electronic switch such as a Mosfet switch. The switch is beneficially controlled by the control system.

The control system is beneficially further arranged to measure a discharge parameter, and the control system is beneficially configured to feedback information regarding the discharge parameter into determination of the treatment energy dose. This provides a benefit in that there is a feedback of a discharge parameter such as the energy output treatment dose from the light emitter meaning that the actual output energy dose can be compared to the calculated energy treatment dose and any error can be compensated. The discharge parameter could be, for example, the output current, or final voltage of the charge storage device. This improves the accuracy of the actual energy output meaning that the apparatus is effectively self-correcting.

The control system may be configured to independently control discharge of each of the individual charge storage elements in the event of provision of a plurality of individual charge storage elements.

In one embodiment the control system is configured to enable energy release from the plurality of charge storage elements sequentially. Alternatively, the control system may be configured to enable energy release from the plurality of charge storage elements substantially simultaneously.

The control system is beneficially configured to at least partially charge the charge storage device to a charge value such as voltage derived from at least one previous operational parameter (e.g. treatment energy dose) of the apparatus. This would mean that a minimum voltage to which the charge storage device could be charged between treatments may be made dependent on previous operation of the apparatus. For example, the charge storage device may be charged to a minimum voltage determined from previous measurements. The minimum voltage could, for example, correspond to the minimum skin tone measured in the last ten treatments thereby effectively reducing the additional charging required for the charge storage device to reflect the voltage required for the next treatment.

The control system is beneficially provided with a memory configured to record a plurality of treatment energy doses output to the light emitting element and further comprises a processor configured to determine the lowest treatment energy output dosage, the control system further configured to charge the charge storage device to the lowest energy output dosage.

Determination of treatment energy setting by the apparatus automatically on the basis of the sensed skin parameter removes the necessity for the user to determine skin tone (or other physical parameter) or take extra steps in the treatment process. However, it is possible that the user would like some level of control over the automatic selection. Any automatic selection of output would be pre-determined to be suitable for the majority of users. However, some users may find the treatment painful (or otherwise too intense), or ineffective, and may desire some manual control. This could be achieved at the same time as automatic selection by allowing the user to select alternative 'ranges' of automatic selection. The apparatus therefore further beneficially includes a user input for changing the treatment energy dose. The user input preferably comprises an override function to the determined treatment energy dose. The treatment energy dose may be increased or decreased. The change in treatment energy dose is preferably predetermined.

A user could select a 'Gentle' mode which reduces the treatment energy dose by a pre-determined amount e.g. the treatment energy dose could be reduced by a fixed value or percentage across the range of determined treatment energy doses. Alternatively, the maximum value of treatment energy dose may be limited.

Alternatively, a user may select an 'Intense' mode which increases the output of the determined treatment energy dose by a pre-determined amount e.g. the energy dose may be increased by a fixed value or percentage across the range of determined treatment energy doses.

The treatment energy dose may be changed dependent on a user selected input parameter comprising a body parameter. This may for example be body location, hair colour, hair thickness etc. The range of treatment energy dose may be changed for improved suitability to the individual user.

The user input may alter another output treatment parameter such as energy dose length or pulse shape.

When utilising the user input for changing the treatment energy dose indication is beneficially provided by the indicator, which is preferably a visual display where a bar of lights may display or display a representation of sensor measurement and/or treatment energy dose which changes if the user input is activated.

The present invention also extends to a method of treating the skin through transmission of light energy to the skin from a light emitting element comprising the steps of:
    measuring a parameter of the skin with at least one sensor;
    configuring a control system to determine a treatment energy dose to be delivered from a charge storage device to the light emitting element using the sensor measurement;
    discharging the treatment energy dose from the charge storage device to the light emitting element to cause light energy release therefrom, and:
    i) terminating discharge of the charge storage device once the treatment energy dose is delivered and/or before discharge is complete; and/or
    ii) providing a plurality of individual charge storage elements and controlling discharge of one or more of the plurality of individual charge storage elements to deliver the treatment energy dose; and/or
    iii) charging the charge storage device in a two or more stage operation wherein the first stage is to an intermediate energy level and the second stage is to an energy level sufficient to deliver the treatment energy dose; and/or
    iv) modulating discharge of the charge storage device to deliver the treatment energy dose.

It will be appreciated that the method of treating the skin may be carried out by a non-medical practitioner and is particularly suitable for home use for the purpose of cosmetic skin treatment and in particular hair depilation.

The present invention also extends to a method of cosmetically treating the skin as hereinbefore described.

The present invention also extends to a method of cosmetic hair depilation as hereinbefore described.

It is extremely important in the present invention that when determining the skin parameters such as skin tone, a robust method of apparatus is utilised since any error could result in an adverse incident meaning the incorrect energy dosage could be applied to the skin. This may result, in the worst case, in damage to the skin through excess treatment energy dose being applied, or alternatively result in an energy dose being too low meaning that the treatment is ineffective.

According to a second aspect of the present invention there is skin treatment apparatus comprising:
- a light source for transmitting an energy dose to the skin;
- at least a first and second sensor, each sensor independently capable of measuring a skin parameter,
- a control system arranged to control operation of the light source in dependence on the first and second sensor measurements.

Such an apparatus provides a simple yet effective manner of determining a skin parameter such as skin tone. The result from the first and second sensors can be used together to determine a more accurate skin parameter with reduced error, thus ensuring accuracy and efficacy of the treatment energy dose.

The apparatus beneficially further comprises a housing for accommodating the light source, the housing having a transmission window for transmission of the energy dose therethrough. The housing is beneficially arranged to accommodate the first and second sensors, the housing including at least one sensor window therein. The relative positions of the transmission window and sensing window are therefore fixed. There is beneficially provided a first sensor window for the first sensor and a second sensor window for the second sensor.

The first and second sensors are beneficially disposed spaced from the transmission window.

Although it is considered possible to determine a skin parameter on the exact area of the skin to be treated, this is difficult to achieve due to the optics required being complex and the measurement system having to be resistant to high energy light treatment doses. As such, the first and second sensor windows are disposed spaced from the transmission window. There are, therefore, provided at least two sensing zones each capable of independently measuring a skin parameter. The skin parameter is usually skin tone and this is achieved by transmitting sensing radiation onto the skin and receiving reflecting radiation from the skin surface. The intensity of the received radiation is representative of the tone of the skin.

The housing beneficially comprises a user contact element defining the transmission window and the first and second sensor windows, the first and second sensors being disposed adjacent the transmission window in the user contact element. The user contact element may comprise a plate. The plate may be planar or may be curved in profile. The transmission window may comprise an aperture in the user contact element. There may be a transparent window provided in the housing intermediate the skin and the light source, however, it will be appreciated that this is not essential. The transmission window may be defined by a recess provided in the housing defined by a peripheral edge of the housing.

The transmission window beneficially partially bridges the linear separation between the first and second sensor windows. The first and second sensors are therefore beneficially placed either side of the window. The remainder of the bridge may be made up of a housing portion and in particular a peripheral edge of the housing defining the transmission window and the first and second sensors. This bridge is minimised to improve accuracy in respect of representative skin parameter of the treatment area.

The control system beneficially comprises a processor configured to calculate from the first and second sensor measurement the treatment energy output.

The control system may be beneficially configured to determine a valid skin parameter reading. This may be determined by the difference between the two sensor measurements being below a predetermined threshold.

In one embodiment the processor is configured to determine a skin parameter measurement that is determined to be the safest or best treatment setting to be used. For example, the safest treatment energy setting would be on the lowest skin parameter measurement from the two sensors. Alternatively, the highest measurement, the average or another calculation could be used.

Aspects of the present invention will now be described by way of example only with reference to the accompanying drawings in which:

DETAILED DESCRIPTION OF THE INVENTION

Figure 3A:
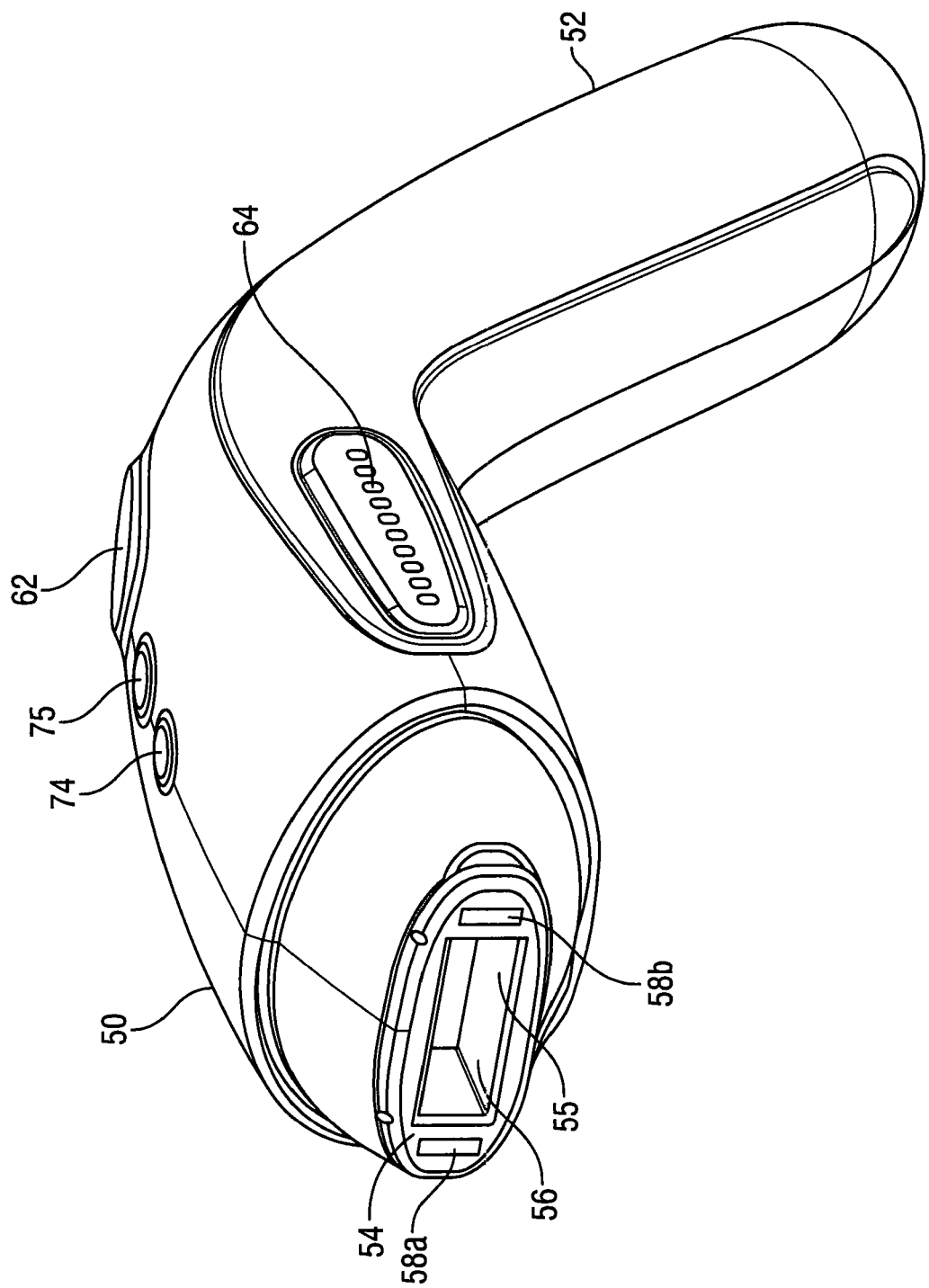
FIG. 3A is a schematic perspective view of an apparatus according to an exemplary embodiment of the present invention.
Figure 3B:
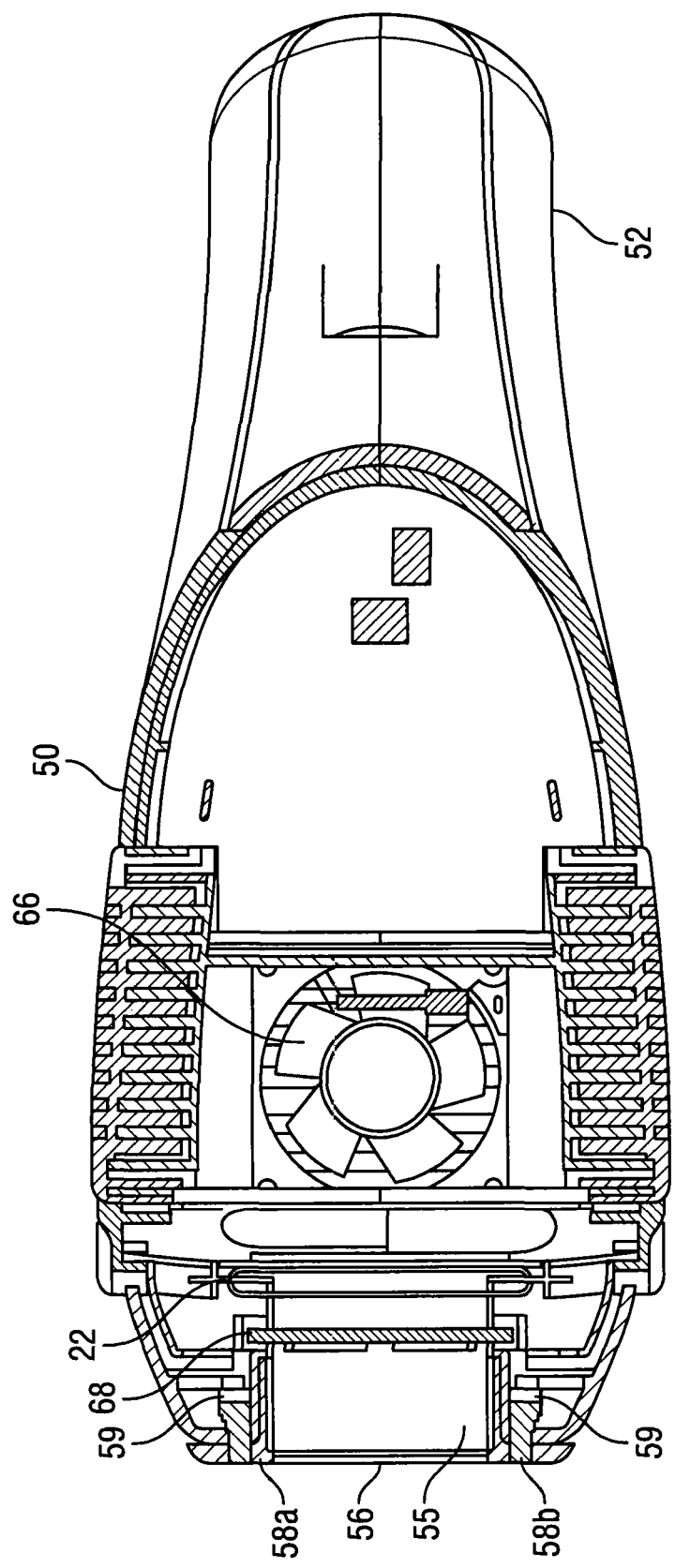
FIG. 3B is a schematic cross-section of the apparatus of FIG. 3A.
Figure 3C:
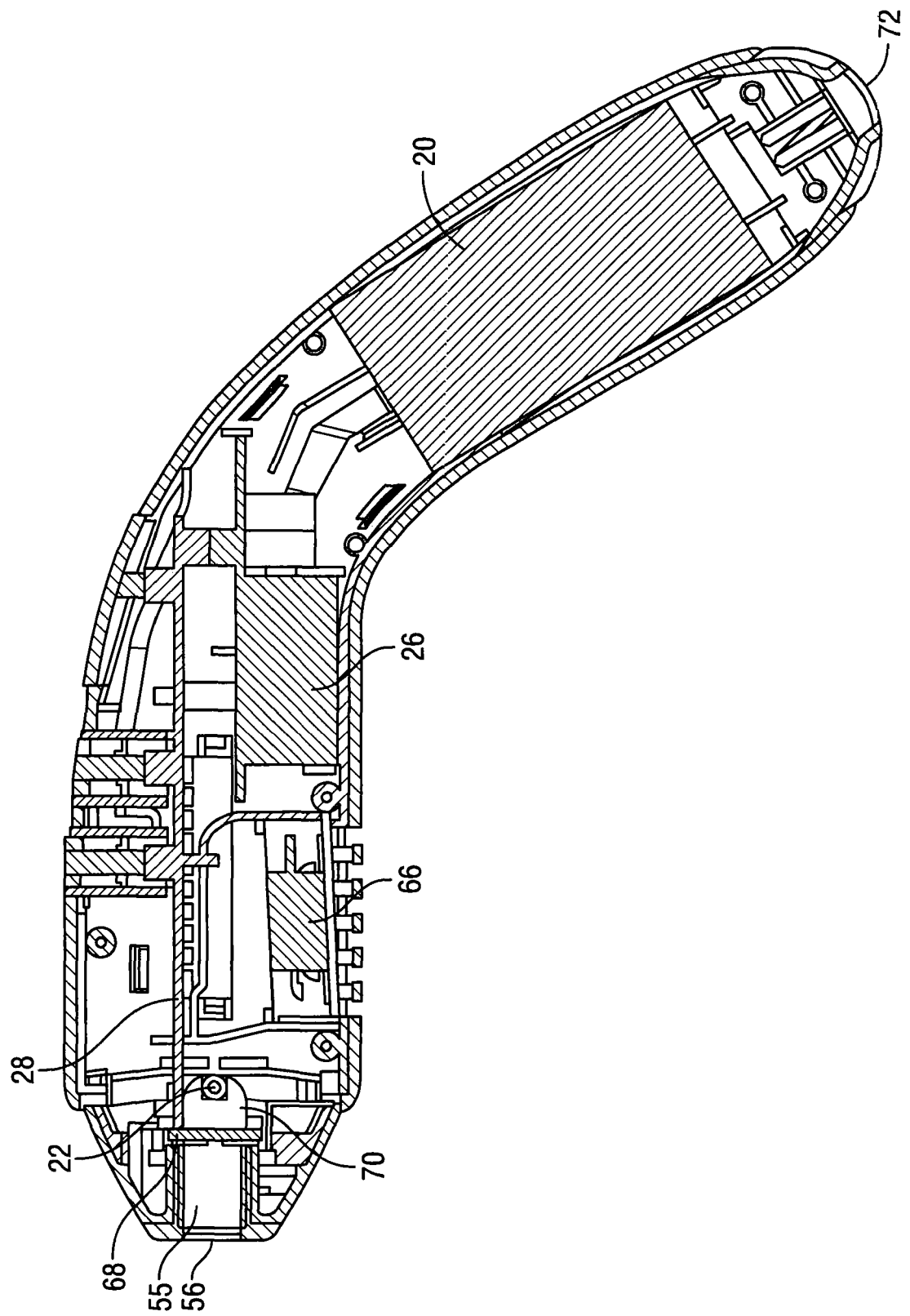
FIG. 3C is a schematic cross-section in the axis perpendicular to the view of FIG. 3B.

According to an embodiment of the present invention as represented in FIGS. 3A-3C a housing in which both the sensor(s) and the light emitting element such as a discharge lamp are located is presented. Referring to FIGS. 3A-3C, there is presented a skin treatment apparatus comprising a housing (50) according to an exemplary embodiment of the present invention that may be used for treating skin disorders and conditions, and even more beneficially is suitable for cosmetic purposes such as hair depilation. The housing (50) comprises a light emitting element (22) accommodated by the housing such as a discharge lamp or flashlamp. The discharge lamp is arranged to generate high intensity pulses of optical radiation. The housing (50) comprises a handle (52) meaning that the housing (50) can be manipulated to be positioned appropriately on the user. The housing (50) includes a skin contact element (54) arranged in use to be positioned adjacent or on preferably a user's skin. The skin contact element (54) includes a light output aperture (56) or transmission window to enable the passage of high intensity pulses of optical radiation therethrough. The cross-sectional area of the light output aperture (56) is effectively the treatment area. The skin contact element (54) further includes first and second sensor windows (58a, 58b) through which a parameter of the skin is determined such as the skin tone. The skin contact element (54) is provided on a head (60) which tapers inwardly towards the skin contact element (54). An actuator (62) is provided for the user to cause release of energy from the charge storage device such as a capacitor (20) which may be in the form of a trigger and cause a pulse of optical radiation to the emitted from the flashlamp (22). A visual indicator (64) is provided to visually show a user the relative power level to which the skin is to be subjected.

Figure 2:
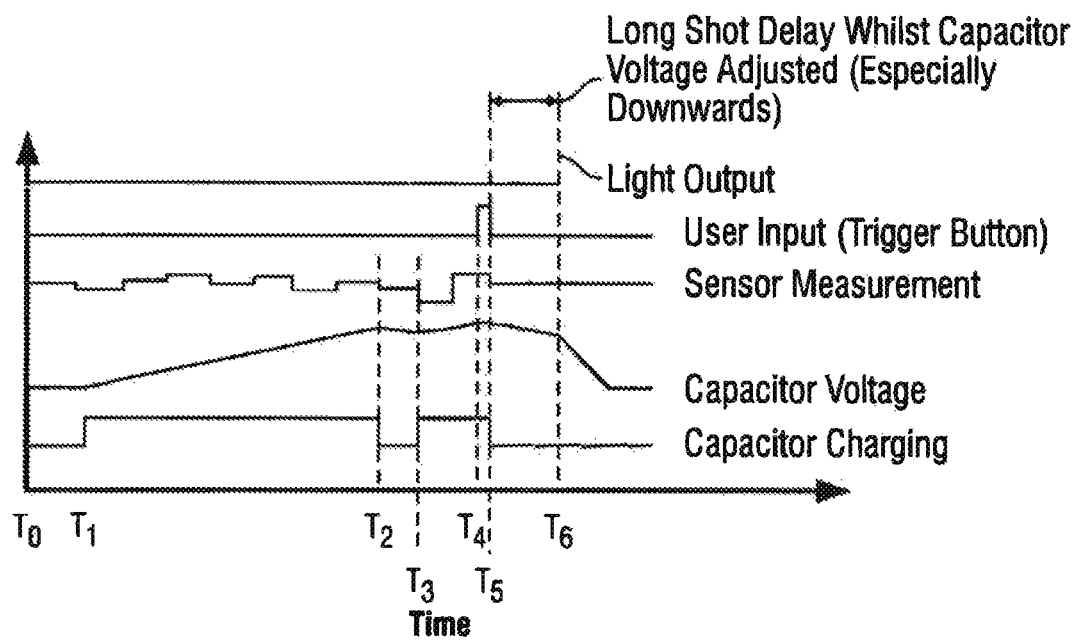
FIG. 2 is a schematic representation of light output, user input, sensor measurement, capacitor voltage and capacitor charging over time for an apparatus considered by the applicant. This demonstrates the possibility of a significant delay occurring between time T5 and T6 whilst the capacitor voltage is adjusted, particularly downwardly.

Referring to FIG. 3B, a transverse cross-section of the housing (50) is presented again showing the handle (52), light output aperture (56) and sensor windows (58a, 58b). Further shown is a fan (66) for cooling of the control circuit (28) on the main printed circuit board. FIG. 2B shows the lamp (22) secured in the housing (50). A filter (68) is provided to filter out ultra-violet light from transferring from the lamp (22) to the skin. A treatment light pulse generated by the lamp (22) passes through the filter, through the light output aperture (56) and onto the skin of a user.

Referring in particular to FIG. 3C, a cross-sectional view is taken on an axis substantially perpendicular to the view of FIG. 3B. Represented in FIG. 3C is the charger circuit (26), control circuit (28) mounted onto a printed circuit board, lamp (22), filter (68) and light output aperture (56). Further shown is a reflector (70) for reflecting the pulse of optical radiation and accommodated within the handle portion (52) of the housing (50) is the energy storage device comprising a capacitor (20). The handle defines an opening (72) for mains power input. The housing (50) as a whole may be stored on a docking station or support as appropriate not shown in the Figures.

The apparatus effectively functions in two modes, a sensing mode and a treatment mode, and the control circuit (28) is configured to enable switching between the two modes. A standby or ready user operable input (74) is provided to ready the apparatus for the user in a sensing mode. There are provided sensors (59) as represented, for example, in FIG. 2B for sensing a measurable skin parameter such as a tone or colour of the skin to be treated. Alternative or additional skin parameters may be sensed. The sensor (59) includes a transmitter arranged to transmit sensing radiation through the sensor window (58a, 58b) onto the skin to be treated. The sensor (59) further includes a receiver such as a photodiode arranged to receive radiation reflected from a skin surface. Intensity of the received radiation is found to be representative of the tone of the skin, for example a light skin tone will reflect more than a dark skin tone. The intensity of the received radiation can be processed by the control circuit (28) using a processor provided thereby and compares the intensity of the calibrated set of intensity measurements to determine a sensed skin tone, which is then stored in a memory of the control circuit. The treatment light pulse energy then outputted to the skin is dependent on the sensed skin tone thus ensuring optimised treatment.

An indicator (64) is preferably provided in the form of a visual display representative of the sensor measurement and/or the treatment energy dose. This may be in the form of a plurality of light indicators which are lit where the number of lights on represents the intensity of energy to be output.

An important feature of the apparatus is the ability for a user to manually override the treatment energy dose determined on the basis of the sensor measurement. This is important in the event a user may find the treatment painful or ineffective and may therefore desire some manual control. A user input is therefore beneficially provided which causes adjustment to the determined treatment energy dose which is preferably carried out by the control system. This effectively changes the treatment energy dose which may be increased or decreased. The increase or decrease may be automatically determined or may be selected dependent on a body parameter such as location and actuation of the user input may reduce the treatment energy dose by a fixed value or percentage or alternatively may limit the maximum value of treatment energy dose. In the alternative a user may select an intense mode which increases the output of the determined treatment energy dose by a predetermined amount. It is beneficial that the indicator (64) provided on the apparatus indicates the selected mode of operation meaning that the beneficially visual indication shows that either intense or a gentle mode or operation has been selected.

Referring to FIGS. 3A to 3C it will be appreciated that in one aspect of the present invention there is provided a skin treatment apparatus which provides improved accuracy in detection of the skin tone for the treatment area. The configuration of providing more than one sensor (59) provides the benefit that a cross-check is provided to ensure that there is accuracy of sensor functioning and further that the treatment area and the skin tone thereof is accurately reflected in the skin tone determined by the sensors. The sensors are provided adjacent the light output aperture (56)

which means that the sensors are not impeded or affected by the high energy intense pulsed light treatment. The sensors (59) are disposed either side of the light output aperture (56) of the skin contact element (54) and each sensor (59) independently records the skin tone. The processor in the control circuit is configured to determine whether a valid skin tone reading has been achieved. This may be in one embodiment determined by the difference between the two skin tone measurements being below a predetermined threshold value. The two skin tone measurements can also be used in determining the safest or best treatment setting to be used. For example, the safest treatment setting would be based on the lowest skin tone measurement from the two sensors. Alternatively the highest measurement, the average or another calculation could be used. It will further be appreciated that additional sensors may be provided to improve accuracy of the determined skin tone of the treatment area.

Embodiment 1

Figure 1A:
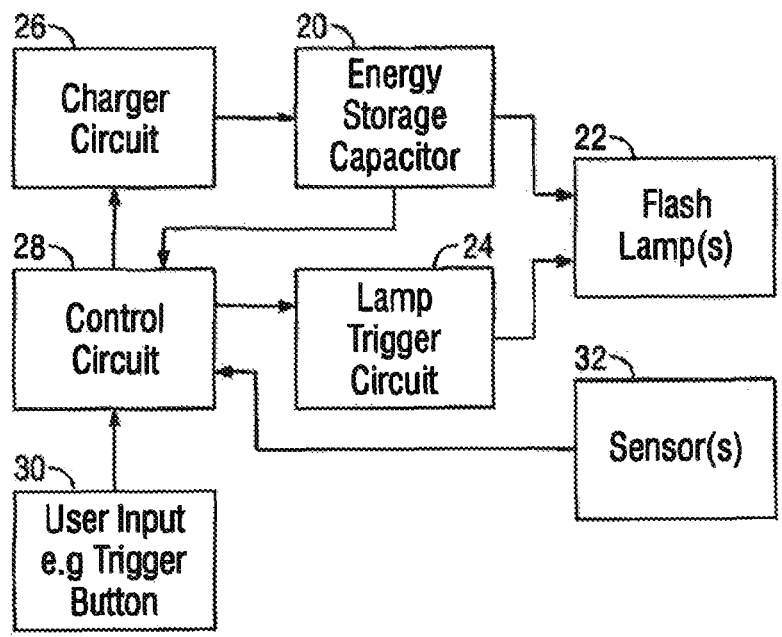
FIG. 1A represents a schematic block diagram of a prior art intense pulsed light (IPL) system.
Figure 1B:
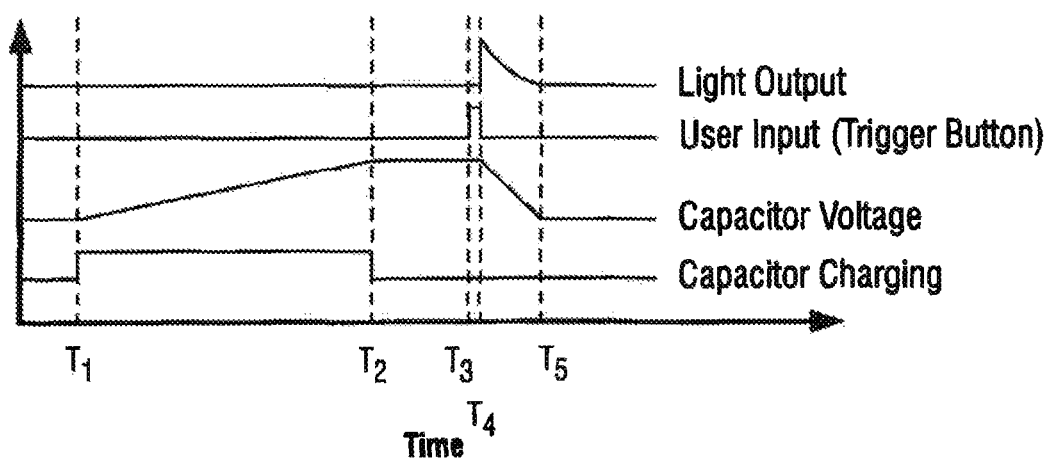
FIG. 1B represents how the light output, user input, capacitor voltage and capacitor charge change over time according to a known system.
Figure 1C:
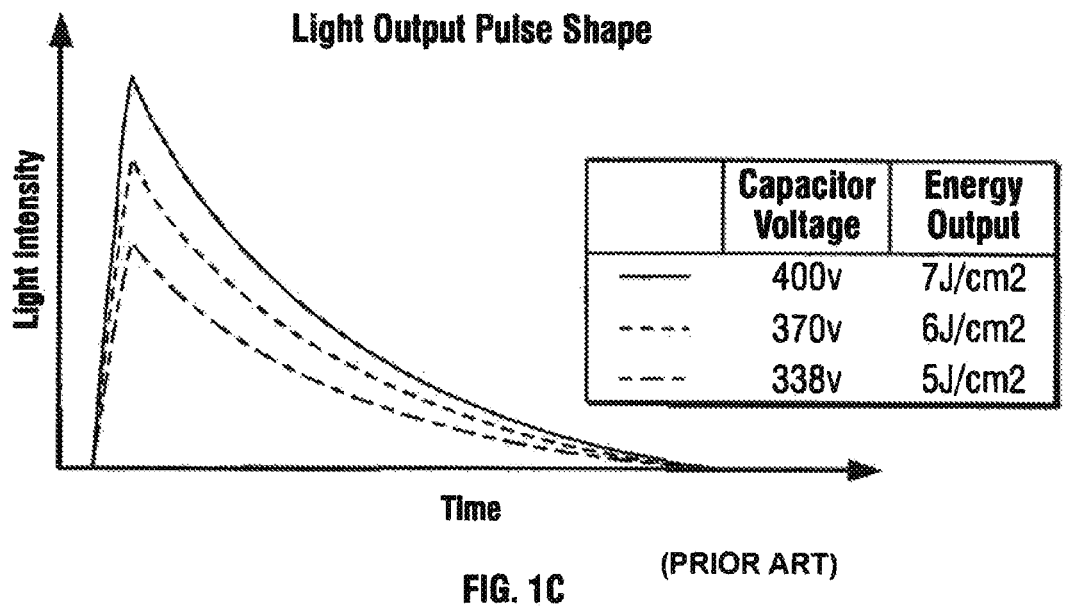
FIG. 1C represents the light output pulse shape for different capacitor voltages and the associated energy output with a graphical representation of light intensity versus time.
Figure 4A:
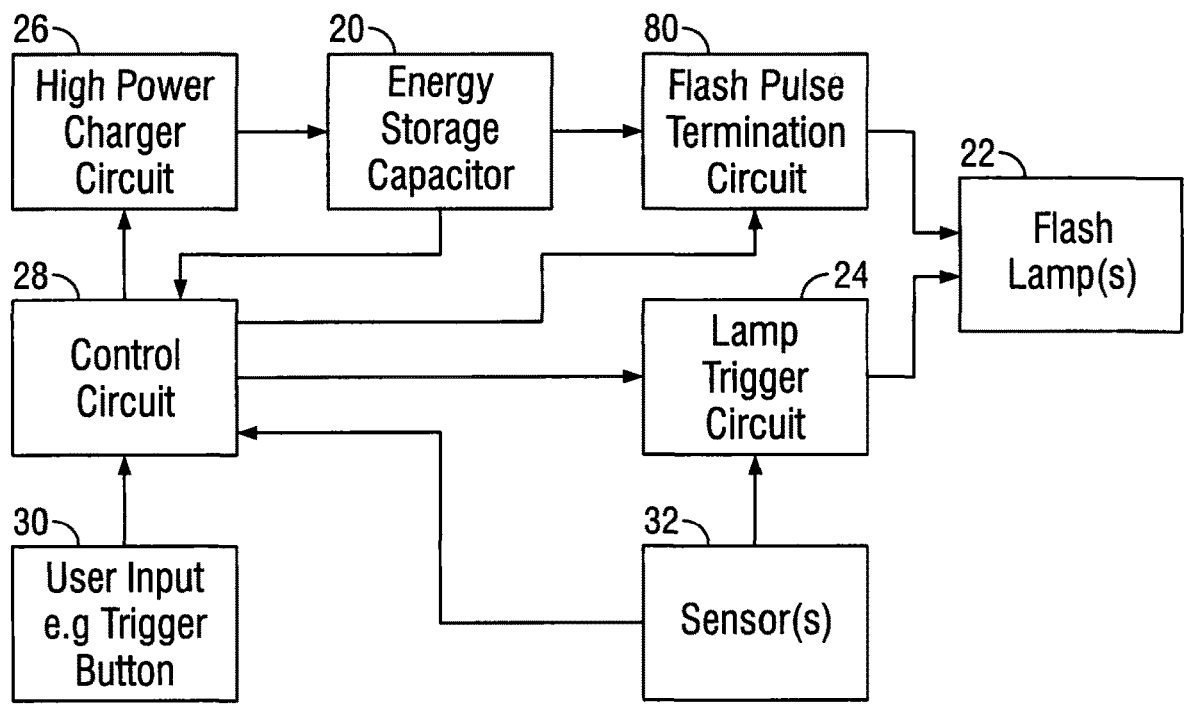
FIG. 4A is a schematic block diagram of components incorporated into the apparatus as represented in FIGS. 3A to 3C.
Figure 4B:
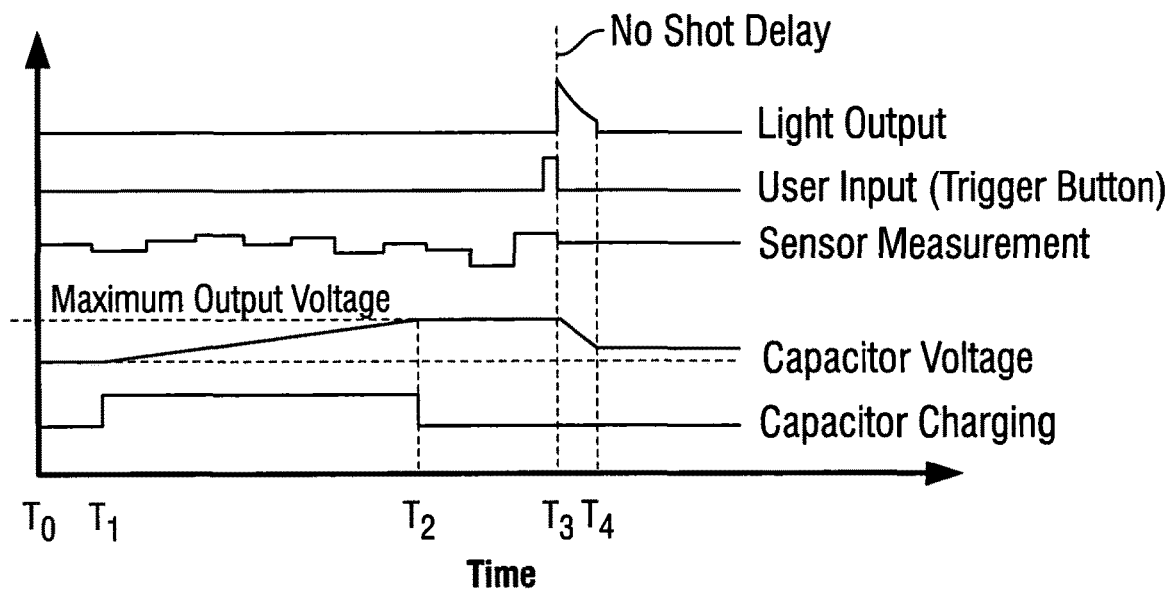
FIG. 4B is a schematic representation of the light output, user input, the sensor measurement, the capacitor voltage, and the capacitor charging over time according to one exemplary embodiment of the present invention.
Figure 4C:
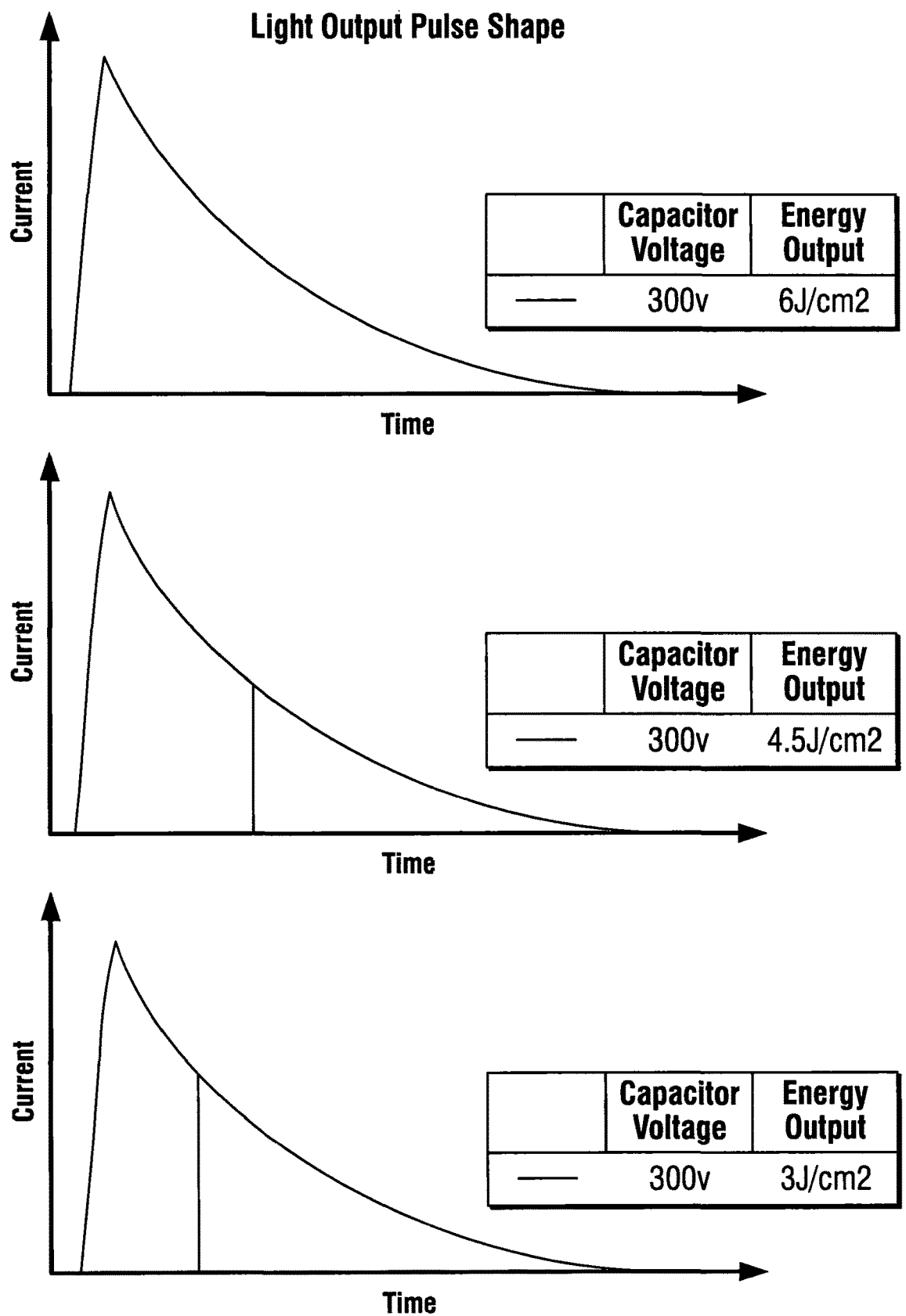
FIG. 4C shows the light output pulse shape according to one embodiment of the present invention.

Reference is now made to FIGS. 4A to 4C. FIG. 4A shows in block diagram form components utilising a first embodiment of the present invention. The diagram is similar to the diagram of FIG. 1A, and like components have been identified with the same reference numerals. It should be noted, however, that in this embodiment there is the additional component of a discharge control element (80) such as an electronic switch (e.g. Mosfet) which may be provided in a flash pulse termination circuit as identified in the block diagram which is arranged to terminate discharge energy from the energy storage device (20) to the flashlamp (22). The effect of the provision of a discharge control element (80) in the flash pulse termination circuit (80) is that the light output pulse shape as shown in FIG. 4C can be terminated in order that a desired energy output is achieved. It will be appreciated that this is irrespective of the initial voltage of the energy storage device. In FIG. 4C the voltage of the energy storage device is 330 volts, however, the energy output for each of the three light output pulse shapes is different dependent on when, over time, the energy output from the energy storage device (20) is terminated. The first graph represents no termination of the energy from the energy storage device (20) and as such the energy output of 6 J/cm$^2$ for a capacitor voltage of 300 volts is maximised. However, the second graph shows termination of the energy transferred from the energy storage device (20) meaning there is a reduced energy output of 4.5 J/cm$^2$. A third graph shows an earlier termination where the energy is 3.6 J/cm$^2$. Again, it is important that the energy output is being controlled irrespective of the initial voltage of the energy storage device (20). This means that the energy storage device (20) can be charged independently of the sensor or sensors output, so can be charged at the same time as the sensor(s) are recording skin tone. As there is no requirement to reduce the charge on the charge storage device (20), there is no associated time delay.

Represented in FIG. 4B is the light output, user input, sensor measurement, capacitor voltage and capacitor charge over time. At time T0 the apparatus is switched on and at time T1 user input (75) may be depressed to cause the apparatus to enter an active mode wherein the sensor measurement commences at T0. At T1 the control system causes capacitor charging and thus the capacitor voltage increases between T1 and T2. During this time the repeated sensor measurement is carried out and skin tone readings are recorded at regular intervals. This is caused by minor movement of the apparatus on the skin. At time T2, the capacitor has been charged to a maximum output voltage such as, for example, 300 volts as represented in FIG. 4C. The capacitor voltage is maintained at this voltage between times T2 and T3 irrespective of the change in skin tone recorded by the sensors. A user input comprising, for example, a trigger is activated and there is immediate light output from the light emitter on input of the trigger by the user. This is important meaning that there is no time delay between user actuation of the apparatus and the treatment energy dose being measured and as such the user is aware that the treatment has taken place and there is no delay time during which time there could have been movement of the apparatus. The capacitor voltage is therefore decreased as the energy is output to the discharge lamp, however, as the energy leaving the capacitor is terminated at a time wherein the desired energy dose has released then the capacity retains a residual voltage and is ready for repeated use. The apparatus is then relocated onto another portion of the skin as appropriate and the process is repeated. As such, the energy output can be determined through the control circuit on the basis of the information received from the sensor but control of the energy output is made through control of the energy released from the energy storage device (20). The energy storage device and charge thereon is therefore not dependent on the sensor input.

In addition to the flash pulse termination circuit through provision of a discharge control element there may be a discharge control element which is configured to modulate the pulse width which has the effect of controlling the capacitor discharge. This may be achieved again from an electronic switch such as a Mosfet switch. This has the effect of increasing the time over which the energy output is provided thereby.

Embodiment 2

In a second embodiment of the present invention, the energy storage device may include a plurality of individual storage device elements such as individual capacitors. The control circuit (28) is arranged to control discharge of the plurality of individual charge storage elements, and may independently control discharge of each of the individual charge storage elements. Release from the charge storage elements may be enabled by the control system sequentially or simultaneously. This may be achieved through the provision of an energy storage device switching circuit (82) which may be termed a capacitor switching circuit. The energy output as identified in FIG. 5C can be manipulated as required dependent on the sensor input to the control circuit (28) without the requirement to charge the multiple energy storage capacitors as a result of the input from the sensor (32). The multiple energy storage capacitors may be charged to, for example, 400 volts as represented in FIG. 5C. The total energy output may be adjusted by selectively choosing how many capacitors to discharge. For example, for a two energy pulse system with two capacitors, the total energy could be rapidly halved or doubled using only one or both of the capacitors. A higher resolution could be achieved by using more capacitors. Alternatively, the time between releases of individual capacitor pulses may be utilised to adjust the treatment intensity. Pulses that are close together are more intense resulting in higher skin and hair temperature than pulses which are further apart thus meaning that energy output is manipulated. As graphically represented in FIG. 5C the energy output can be adjusted dependent on the total capacitance. It will further be appreciated that the individual capacitors can be charged to or be capable of being charged to different voltages in order that appropriate treatment energy doses can be achieved.

Figure 5A:
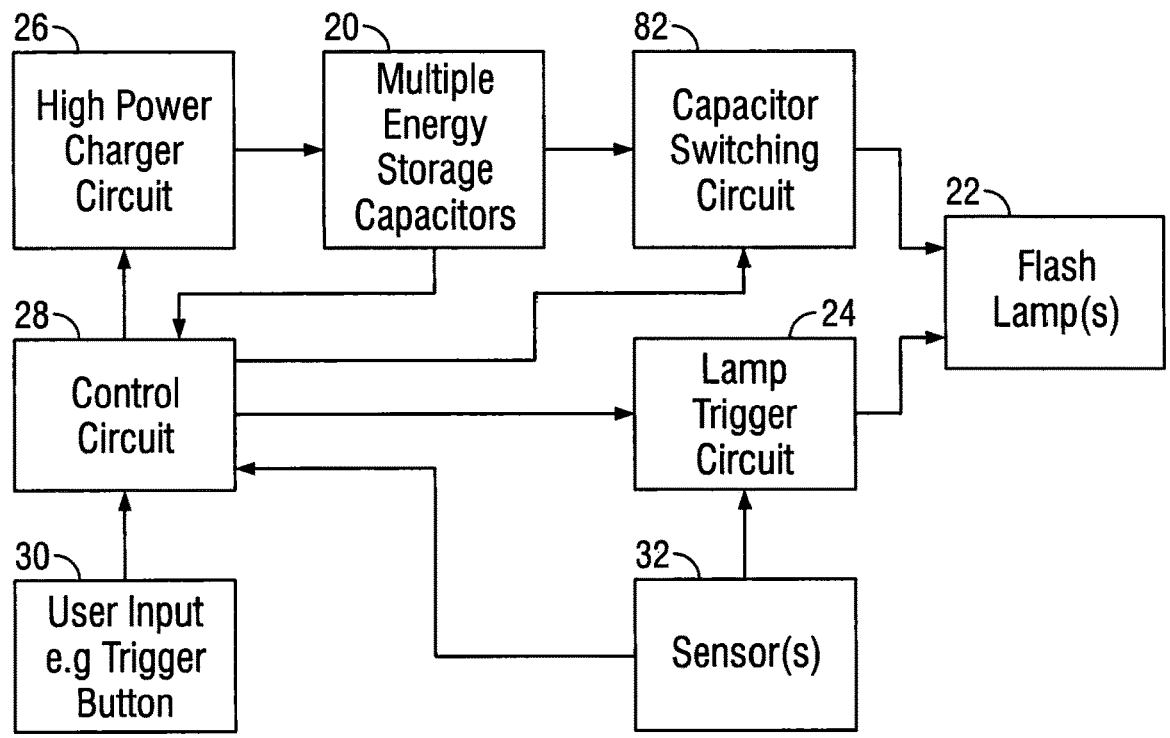
FIG. 5A is an alternative embodiment of the present invention showing the main components of the apparatus of FIG. 3A.
Figure 5B:
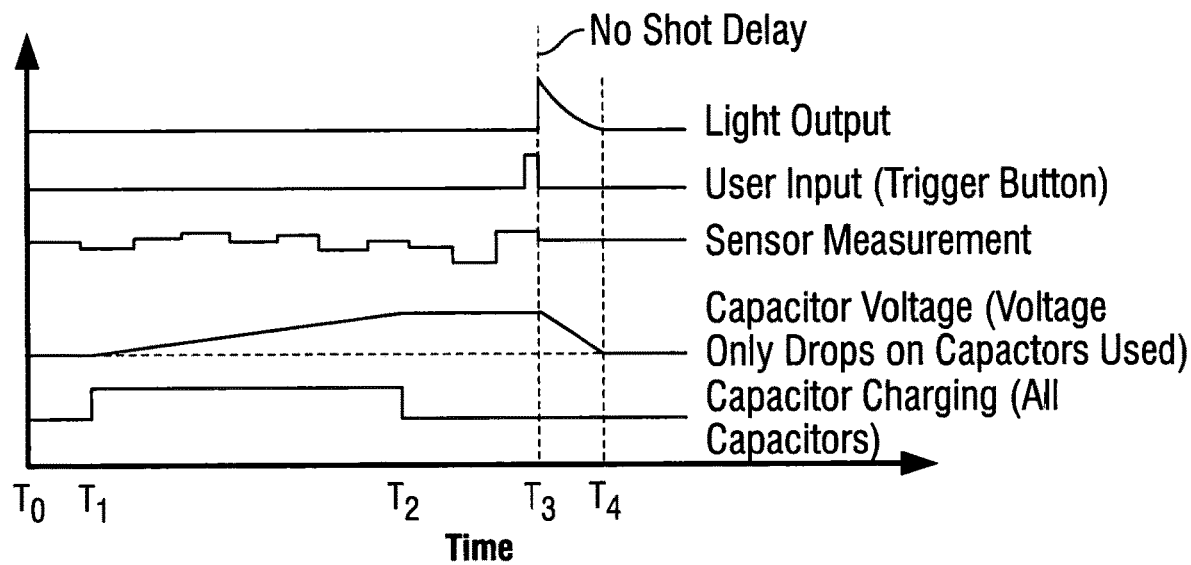
FIG. 5B again shows the light output, user input, sensor measurement, capacitor voltage and capacitor charger according to this embodiment of the present invention.
Figure 5C:
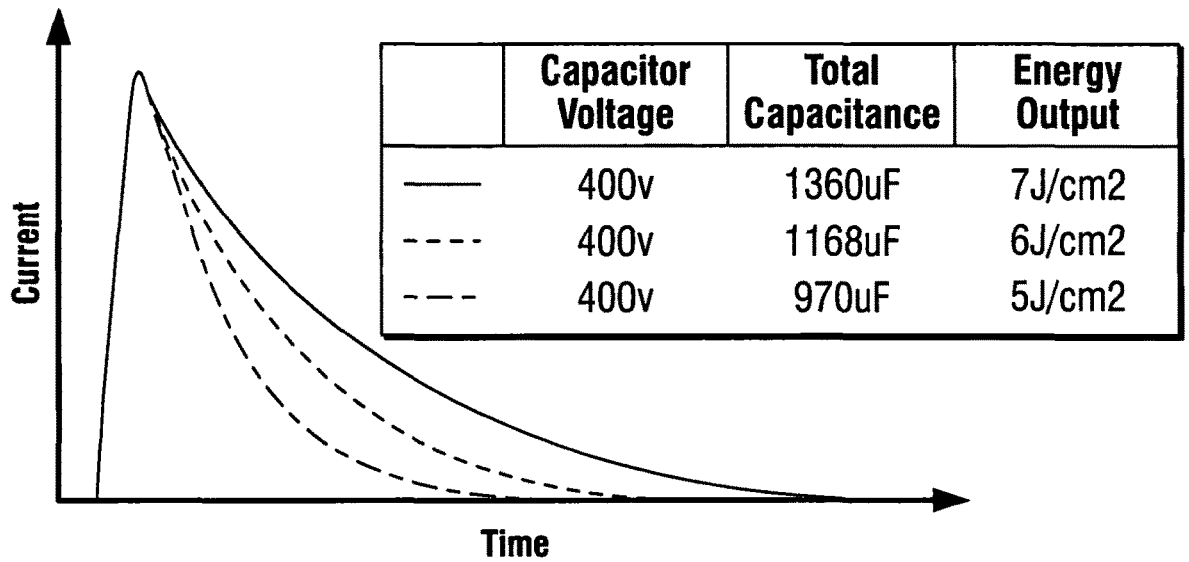
FIG. 5C shows the light output pulse shape according to this embodiment of the present invention.

Referring to FIG. 5B at T0 the apparatus is switched on and at time T1 the user inputs to the apparatus by user input (75) that they wish the apparatus to enter the operative condition. At T1 a valid sensor measurement has been recorded meaning that the capacitor voltage on the multiple capacitors increases between T1 and T2. During this time the sensor measurement may be changing dependent on the recorded skin tone. The user trigger input is activated and there is immediate light output at T3. Between T3 and T4 the light has been output and the capacitor voltage on the capacitors used drops back to the initial level whilst any capacitor that is not used retains its previous voltage.

Embodiment 3

Figure 6A:
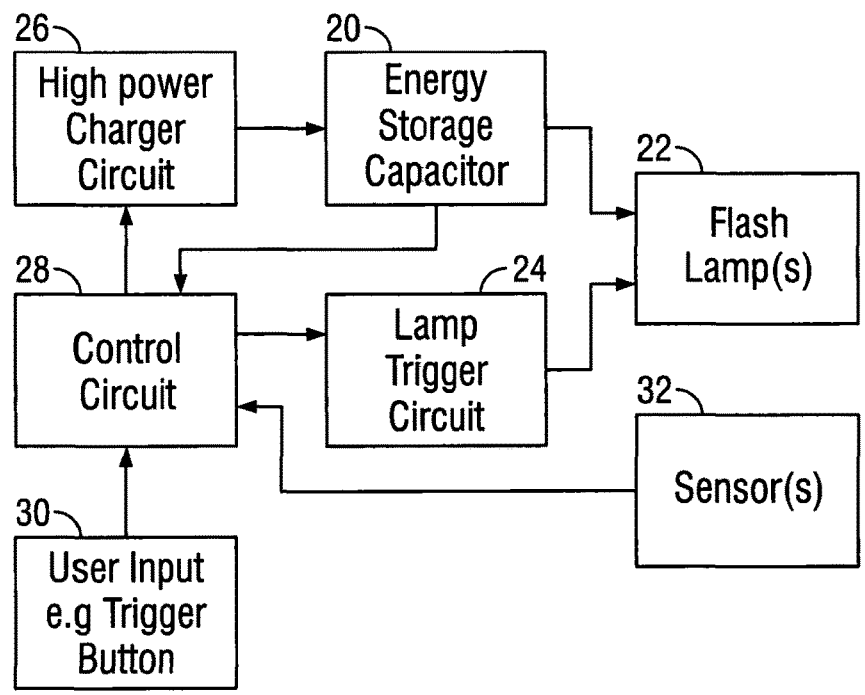
FIG. 6A is a further alternative embodiment of the present invention showing the components that may be incorporated into the apparatus of FIG. 3A.
Figure 6B:
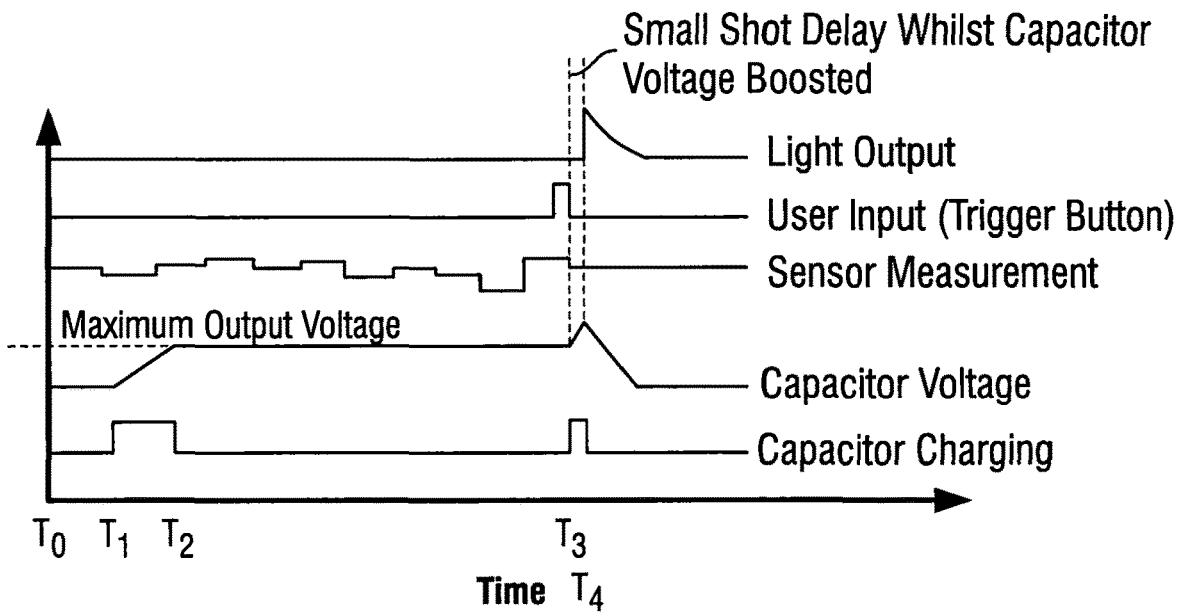
FIG. 6B shows the light output, user input, sensor measurement, capacitor voltage and capacitor charging according to this exemplary embodiment of the present invention.
Figure 6C:
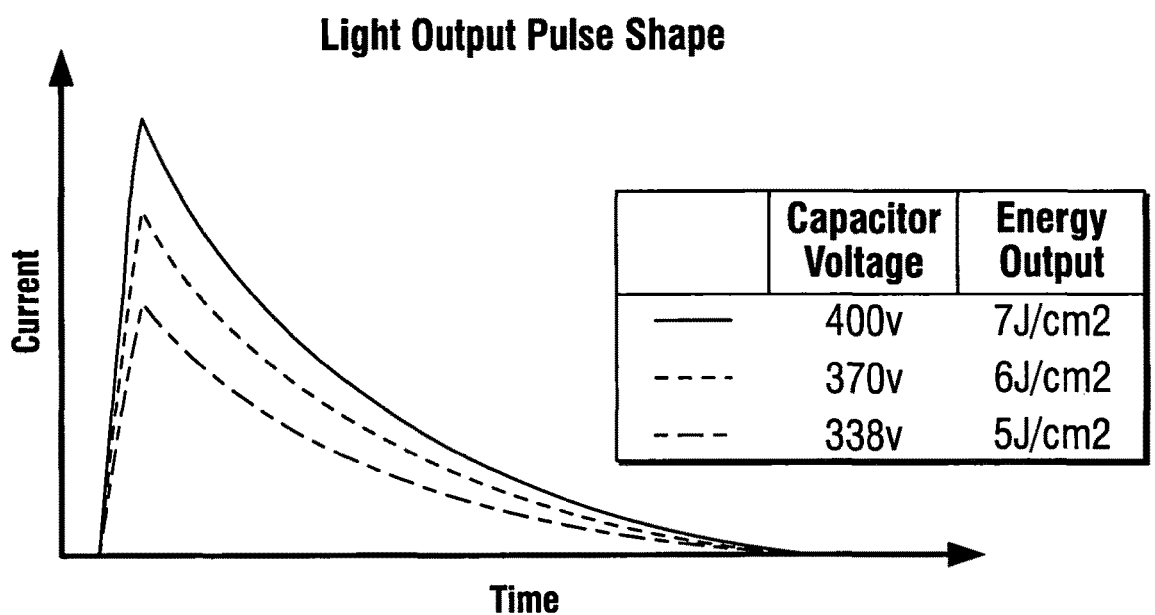
FIG. 6C shows the light output pulse shape achieved in this exemplary embodiment of the present invention.

Referring now to FIGS. 6A to 6C, a third exemplary embodiment of the present invention is presented and again, like components have been presented with the same reference numerals. In one embodiment of the present invention in order to minimise the time delay between user input and their desire to activate the apparatus and the actual light output, the energy storage device (20) can be charged to an intermediate value. This may be independently of the input of the sensor (32). Charging is carried out to a predetermined intermediate voltage and this voltage can effectively be topped up dependent on the skin tone determined by the sensor at the time the user activates the input. As such in this embodiment the energy storage device (20) may be charged independently of the sensor input to a voltage of, for example, 300 volts and this voltage can be boosted dependent on the skin tone measurements. At T0 as represented in FIG. 6B, the device is switched on and at T1 a user input causes activation of the apparatus. Sensor measurements are recorded and at T1 the energy storage device (20) is charged to a predetermined minimum voltage. This is maintained at time T2 until a user input through the trigger button actuates the apparatus. On the basis of this input and the sensor measurement at time T3, the energy storage device is boosted and at this time the voltage increases and the energy storage device is charged. At T4, therefore, the light is output as a pulse and the voltage of the energy storage device (20) drops. Through testing it has been determined that the energy storage device can be charged from the intermediate voltage to the maximum required output voltage in approximately 200 msec. However, it will be appreciated that, in order to achieve this, a very high power charger is required. FIG. 6C shows the light output pulse shave achieved in the apparatus of FIG. 6A.

As a modification of this embodiment, it is noted that in general a person's skin tone does not vary by more than one or two grades on a six-grade system such as Fitzpatrick. This is within a normal treatment zone, for example, on a leg. Therefore, the control system may store previous skin tone measurements on a minimum voltage that the energy storage device is charged to between uses that could be determined from the previous measurements. For example, the minimum voltage could correspond to the minimum skin tone measured during the last ten uses.

Embodiment 4

In a fourth embodiment of the present invention the control system is arranged to modulate discharge of the energy storage device to deliver the treatment energy dose. This may be achieved through the provision of the discharge being provided through a pulse width modulation (PWM) circuit using an electronic switch such as a Mosfet. This has the effect of controlling the energy pulse shape and as such the energy pulse may be changed meaning that the output to the light emitting element is controlled so as to be 'slower' meaning that the light remains activated for longer and as such the intensity of light on the skin is reduced. The output energy may be manipulated to provide a number of alternative pulse shapes. This means that effectively the energy output can be maintained the same, however, the time period over which the energy is supplied is extended and as such the intensity on a user's skin is reduced. This means that the discharge of the energy from the charge storage device is modulated to achieve the determined treatment energy dose and as such the charge storage device does not have to be adjusted dependent on the current sensor reading.

It will be appreciated that the control system may modulate discharge of the charge storage device in any of the embodiments as desired.

Aspects of the present invention have been described by way of example only and it will be appreciated by the skilled addressee that modifications and variations may be made without departing from the scope of protection afforded by the appended claims.

The invention claimed is:

1. A skin treatment apparatus comprising:
   a light source comprising a light emitting element for transmitting light energy to a skin and a capacitor for discharging an energy dose to the light emitting element;
   at least one sensor for measuring a parameter of the skin, the capacitor configured to be charged from a power input independently of the measurement from the at least one sensor; and
   a control system configured to determine a treatment energy dose to be delivered, the treatment energy dose being optimized using a measurement from the sensor, the control system further configured to start delivery of the treatment energy dose based upon a user input and then to terminate discharge of the capacitor upon delivery of the treatment energy dose before discharge of the capacitor is complete.

2. A skin treatment according to claim 1, further comprising a housing arranged to accommodate the light emitting element and the sensor.

3. A skin treatment apparatus according to claim 1, wherein the control system is configured to control charging of the capacitor prior to and/or at the same time as determination of the treatment energy dose.

4. A skin treatment apparatus according to claim 1, wherein the control system is configured to enable charging of the capacitor and/or one or more individual charge storage elements to a pre-determined voltage.

5. A skin treatment apparatus according to claim 1, wherein:
   in operation the sensor is configured to record multiple skin parameter measurements prior to determination of the energy dose; and/or
   the control system is configured to determine the treatment energy dose based on a plurality of the multiple skin parameter measurements.

6. A skin treatment apparatus according to claim 1, further comprising an energy modulation arrangement configured to modulate a supply of the treatment energy dose to the light emitting element.

7. A skin treatment apparatus according to claim 1, wherein:
the control system includes a discharge control element operable to terminate the energy dose supplied from the capacitor, and/or
the discharge control element includes a switch.

8. A skin treatment apparatus according to claim 1, wherein the control system is configured to measure a discharge parameter and to feedback the discharge parameter into the determination of the treatment energy dose.

9. A skin treatment apparatus according to claim 1, wherein the control system is configured to enable partial charging of the capacitor independently of the measurement from the sensor.

10. A skin treatment apparatus according to claim 1, wherein the capacitor comprises a plurality of individual charge storage elements and the control system is configured to selectively discharge one or more of the plurality of individual charge storage elements to deliver the treatment energy dose.

11. A skin treatment apparatus according to claim 1, wherein:
the capacitor comprises a plurality of individual charge storage elements; and
the control system is configured to enable discharge from the plurality of the individual charge storage elements sequentially; or
the control system is configured to enable discharge from the plurality of the individual charge storage elements substantially simultaneously.

12. A skin treatment apparatus according to claim 1, wherein the control system is configured to partially charge the capacitor dependent on the measurement from the sensor.

13. A skin treatment apparatus according to claim 1, wherein the control system is configured to at least partially charge the capacitor to a voltage derived using at least one previous operational parameter of the apparatus.

14. A skin treatment apparatus according to claim 13, wherein the control system is provided with a memory configured to record a plurality of treatment energy doses output to the light emitting element and a processor configured to determine the treatment energy output dosage, the control system configured to charge the capacitor to the lowest energy output dosage.

15. A skin treatment apparatus according to claim 1, further comprising a user operable input for changing the treatment energy dose.

16. A skin treatment apparatus according to claim 15, wherein the user operable input is configured to cause a change to the treatment energy dose by one or more pre-determined values.

17. A skin treatment apparatus according to claim 15, wherein the user operable input is configured to cause a change of the treatment energy dose dependent on a user selected input body parameter.

18. A skin treatment apparatus according to claim 1, further comprising an indicator for providing information regarding the parameter measured by the sensor and/or the treatment energy dose.

19. A skin treatment apparatus according to claim 1, wherein the measured parameter of the skin is skin tone.

20. A method of treating a skin through transmission of light energy to the skin from a light emitting element comprising the steps of:
measuring a parameter of the skin with at least one sensor;
determining and optimizing a treatment energy dose to be delivered from a capacitor to the light emitting element using the measured parameter by the at least one sensor;
charging the capacitor from a mains or external power input independently of the measurement from the at least one sensor;
starting to discharge the treatment energy dose from the capacitor to the light emitting element to cause light energy release therefrom and emit a single energy dose to the skin based upon a user input;
terminating discharge of the capacitor once the treatment energy dose has been discharged and before discharge of the capacitor is complete; and
recharging the capacitor from the mains or external power input independently of the measurement from the at least one sensor after discharging treatment energy dose from the capacitor.

21. A skin treatment apparatus comprising:
a light source comprising a light emitting element for transmitting light energy to a skin and a capacitor for discharging an energy dose to the light emitting element;
at least one sensor for measuring a parameter of the skin, the capacitor configured to be charged from a mains or external power input independently of the measurement from the at least one sensor; and
a control system configured to determine a treatment energy dose to be delivered, the treatment energy dose being optimized using a measurement from the sensor, the control system further configured to start delivery of the treatment energy dose based upon a user input and then to terminate discharge of the capacitor upon delivery of the treatment energy dose before discharge of the capacitor is complete, and
the skin treatment apparatus is operable according to a charging and discharging cycle of the capacitor, wherein the cycle includes charging the capacitor from the mains or external power input, discharging the optimized treatment energy dose to the light emitting element to emit a single energy dose to the skin and recharging the capacitor from the mains or external power input.

22. A skin treatment apparatus according to claim 1, wherein the measured parameter of the skin is a dose-indicating parameter.

23. A skin treatment apparatus according to claim 1, wherein the capacitor has a residual charge after the discharge is terminated upon delivery of the treatment energy dose.

* * * * *